United States Patent [19]

Thistle et al.

[11] Patent Number: 4,755,167
[45] Date of Patent: Jul. 5, 1988

[54] IN VIVO METHOD FOR DISTRIBUTION AND STIRRING OF THERAPEUTIC AGENTS

[75] Inventors: Johnson L. Thistle, Rochester, Minn.; Mark J. Allen, Kansas City, Mo.

[73] Assignee: Research Corporation, New York, N.Y.

[21] Appl. No.: 599,398

[22] Filed: Apr. 12, 1984

[51] Int. Cl.$^4$ ............................................. A61M 1/00
[52] U.S. Cl. ......................................... 604/28; 604/22
[58] Field of Search ...................... 604/48, 22, 35, 28, 604/152, 150, 51, 49

[56] References Cited

U.S. PATENT DOCUMENTS

| | | | |
|---|---|---|---|
| 1,846,596 | 2/1932 | Hertzberg | 604/152 |
| 2,024,967 | 12/1935 | Dierker. | |
| 3,042,041 | 7/1962 | Jascalevich. | |
| 3,142,299 | 7/1964 | Henderson. | |
| 3,316,910 | 5/1967 | Davis. | |
| 3,329,147 | 7/1967 | Barron. | |
| 3,425,410 | 2/1969 | Cammack | 604/152 X |
| 3,426,743 | 2/1969 | Chestnut et al. | |
| 3,429,313 | 2/1969 | Romanelli. | |
| 3,885,567 | 5/1975 | Ross. | |
| 3,888,994 | 6/1975 | Wagner et al. | |
| 3,892,226 | 7/1975 | Rosen. | |
| 3,955,574 | 5/1976 | Rubinstein. | |
| 4,041,947 | 8/1977 | Weiss et al. | |
| 4,205,176 | 5/1980 | Zestermann et al. | |
| 4,255,096 | 3/1981 | Coker et al. | |
| 4,282,873 | 8/1981 | Roth. | |
| 4,294,251 | 10/1981 | Greenwald et al. | 604/35 X |
| 4,315,506 | 2/1982 | Kayser et al. | |
| 4,447,226 | 5/1984 | Mayoral. | |
| 4,457,755 | 7/1984 | Wilson. | |
| 4,464,399 | 8/1984 | Hofmann. | |
| 4,516,398 | 5/1985 | Wuchinich. | |
| 4,525,156 | 6/1985 | Benusa et al. | |
| 4,526,575 | 7/1985 | Roblejo. | |
| 4,655,197 | 4/1987 | Atkinson | 604/150 X |

FOREIGN PATENT DOCUMENTS 2944782 6/1979 Fed. Rep. of Germany.

OTHER PUBLICATIONS

Y. Takasawa, et al., "A study on the Dissolution and Disintegration of Calcium Bilirubinate Stones, with special reference to effects of Litholytic Agents in Human Bile and to Irrigation of Bile Duct in Dogs", Tohoku J. exp. Med., 1982, 138, 383–395.
U. Leuschner, et al., "Alternating Treatment of Common Bile Duct Stones with a Modified Glyceryl-1-Monooctanoate Preparation and a Bile Acid-EDTA Solution by Masobiliary Tube", Scand. J. Gastroent., 1981, 16, 491–503.
U. Leuschner, et l., "Gallstone Dissolution in the Biliary Tract: in Vitro Investigations on Inhabiting Factors and Special Dissolution Agents", American Journal of Gastroenterology, vol. 77, No. 4, 1982, 222–226.
U. Leuschner, et al., "Biochemical and Morphological Investigations of the Toxicity of a Capmul Preparation and a Bile Salt-EDTA Solution in Patients with Bile Duct Stones", American Journal of Gastroenterology, vol. 77, No. 4, 1982, 291–298.
U. Leuschner, et al., "Dissolution of Bileduct Stones", Letter to the editor, The Lancet, Feb. 7,1981, 336.
International Journal of Clinical Pharmacology, Therapy and Toxicology, vol. 21, No. 1, pp. 37–40 (1983).
International Journal of Clinical Pharmacology, Therapy and Toxicology, vol. 21, No. 2 pp. 95–97 (1985).
U. Leuschner, et al., "The Dissolution of CBD Cholesterol and Pigment Stones with Methyl-Teritiary-butyl-ether (MTBE) in vitro and in vivo, "Gastroenterology, vol. 88, No. 5, Parts 2.
U. Leuschner, et al., "Treatment of Bile Duct Stones by Combined use of Endosceopy and Flushing Therapy", A/S/G/E, vol. 28, No. 2, 1982, p. 137.
U. Leuschner, et al., "Dissolution of Black Pigment Stones (BPS) of the Gallbladder", Gastroentrerology, vol. 88 No. 5, Parts 2.
U. Leuschner, et al., "Our 10 Years' Experience in Gallstones Dissolution, Comparison with the National Cooperative Gallstone Study (NCGS) and the Tokyo Cooperative Gallstone Study (TCGS), Japan".
Hepatology, vol. 3, No. 5, p. 809 (1983).
International Journal of Clinical Pharmacology, Therapy and Toxicology, vol. 19, No. 6, pp. 273–274 (1981).
Br. F. Surg. vol. 68 pp. 203–308 (1981).

Primary Examiner—Stephen C. Pellegrino
Attorney, Agent, or Firm—Scully, Scott, Murphy & Presser

[57] ABSTRACT

Method and means for distributing therapeutic agents in a localized area of a patient's body comprising introducing a therapeutic area of a patient's body and agitating the therapeutic agent in the localized area of a patient's body by introducing an oscillating liquid to the localized area in an amount effective to facilitate distribution of the therapeutic agent therein.

28 Claims, No Drawings

IN VIVO METHOD FOR DISTRIBUTION AND STIRRING OF THERAPEUTIC AGENTS

FIELD OF THE INVENTION

This invention relates to a method and means for thorough distribution or stirring of therapeutic agents in a localized area of a patient's body. More particularly, the invention relates to agitating the therapeutic agent in vivo to facilitate homogenous distribution of the agent or dissolution of a solid or both in a localized area of a patient's body.

BACKGROUND OF THE INVENTION

The effectiveness of therapeutic agents in a patient can depend to a great degree on the therapeutic agent's accessibility to the area of a patient's body to be treated. Therefore, it is highly desirable to accomplish homogeneous distribution of a therapeutic agent within a body space to be treated in order to effectively, efficiently and quickly therapeutically treat the target area. Conventional methods for introducing therapeutic agents to localized areas of the body for treatment provide if at all for only limited homogeneous distribution of the agent.

Dissolution of solids is effectively enhanced by stirring or agitating the solvent within a medium. Agitation permits homogeneous distribution of the agent throughout the medium and in the case of dissolving solid materials in a solvent such agitation increases the rate of dissolution possible with a minimal amount of solvent being used. The use of agitation enhances delivery of therapeutic agents to the desired specific site of action within the human body has obvious practical problems as would be known to those skilled in the art. It is therefore highly desirable to provide a method for distributing therapeutic agents in a localized area of a patient's body to facilitate homogeneous distribution and to improve the efficiency and rate of dissolving undesirable solids that may be in a localized area of a patient's body by a practical and safe method of in vivo agitation.

A good example of the present inability to facilitate distribution of therapeutic agents within the human body is the method conventionally employed for the dissolution of gallstones in vivo by a solvent such a mono-octanoin A conventional method for in vivo gallstone dissolution is to introduce by simple perfusion a solvent such a mono-octanoin into a localized area of the patient's body where the gallstones to be dissolved are located such as in the biliary tract. Conventionally, the perfusion of the solvent such as mono-octanoin for up to three weeks may be required to fully dissolve cholesterol gallstones in the biliary tract. It is postulated that such dissolution could be accomplished more effectively and quickly by improving the distribution of the solvent by agitation in vivo.

SUMMARY OF THE INVENTION

It is therefore an object of the present invention to provide a method for distributing and stirring therapeutic agents in a localized area of a patient's body which would facilitate the homogeneous distribution of the therapeutic agent and increase the effectiveness of the agent therein.

It is a further object of the present invention to provide a method for distributing a therapeutic dissolving agent in a localized area of a patient's body to facilitate dissolving undesirable material residing therein.

To achieve the objects in accordance with the purposes of the present invention as embodied and broadly described herein, the invention comprises a method for distributing therapeutic agents in a localized area of a patient's body comprising: agitating a therapeutic agent introduced to a localized area of a patient's body, the agitation is effected at the localized area by introducing an liquid in an oscillating (to and fro) fashion to the localized area in a manner sufficient to facilitate distribution and stirring of the therapeutic agent in the localized area.

One embodiment of this invention comprises a method for distributing a therapeutic dissolving agent in a localized area of a patient's body to facilitate dissolving undesirable matter residing therein comprising: introducing a therapeutic dissolving agent to a localized area wherein the matter to be dissolved resides; agitating the therapeutic dissolving agent within the localized area by introducing an oscillating liquid to the localized area in an amount effective to stir and diffusingly distribute the dissolving agent; and dissolving the undesirable matter residing in the localized area. The method of the present invention is particularly adaptable for facilitating the dissolution of gallstones in vivo in the biliary tract or gallbladder.

The present invention also relates to pump means for delivering and distributing a therapeutic agent introduced into a localized area of a patient's body, by introducing liquid in an oscillating manner to provide agitation of the therapeutic agent at the localized area. The pump means comprise liquid injecting means; liquid aspirating means; adjusting means to control the volume of the oscillating liquid; separate adjusting means to control the rate of injection and aspiration independently; and forward flow add-on means to increase or maintain the volume of the oscillating liquid. The pump means of the invention are preferably adaptable for diffusing a dissolving agent in a localized area of a patient's body to facilitate dissolving of undesirable matter residing herein.

DETAILED DESCRIPTION OF THE PREFERRED EMBODIMENTS

Reference will now be made in detail to the present preferred embodiments of the method of the invention. The invention provides a method for diffusing a therapeutic agent in a localized area of a patient's body.

It is often desirable to effectively distribute therapeutic agents in certain portions of a patient's body to effectively treat various conditions. Effective and efficient distribution of a therapeutic agent in a localized area of the body has practical advantages, for example, to permit the effective introduction of smaller amounts of expensive or toxic drugs and materials which would otherwise be necessary. Effective distribution of the drug would maximize the effectiveness obtainable at lower levels of and thus improve the treatment in terms of economy or toxicity.

For the purposes of the present invention distribution of a therapeutic agent in a localized area means to spread or diffuse the agent throughout a specific or limited area of a patient's body.

In accordance with the methods of the invention, a therapeutic agent is introduced to a localized area of a patient's body by any conventional means including injection, catheter placement, ingestion, etc. The therapeutic agent thus introduced into the localized area is agitated by introducing an oscillating liquid to the localized area. Alternatively, the oscillating liquid may itself be the therapeutic agent. The oscillating liquid is introduced by various means known to those skilled in the art for introducing liquid into a localized area of a patient's body such as through percutaneous transhepatic catheter placement (PTC); endoscopic retrograde biliary catheter placement; or placement of a T-tube into the localized area by surgical means wherein the source of the oscillating liquid is connected to such introductory means and the oscillating liquid is passed through these means into the localized area. The oscillating liquid is made to oscillate by alternating infusion and aspiration means. Means for oscillating the liquid include a combined aspirating and infusing pump wherein a selected volume of the oscillating liquid is first injected into the localized area and then aspirated from the localized area to produce the desired oscillating effect and agitation therein. The agitation of the therapeutic agent diffuses the agent within the area and improves its effectiveness therein. For the purposes of the invention, the terms injecting and infusing are interchangeable.

The oscillating liquid may either be separate from the therapeutic agent or may contain the therapeutic agent therein or may substantially comprise the therapeutic agent or solution or mixture thereof. The oscillating liquid can comprise any liquid of sufficient viscosity and density to create agitation effective to facilitate distribution of the therapeutic agent in the localized area. Suitable oscillating liquids would include water, organic solvents, solvents for the therapeutic agent, or therapeutic liquids which dissolve undesirable materials such as for example, solvents for dissolving gallstones.

The oscillating liquid can be injected and aspirated at various rates although it has been found to be particularly effective for dissolving foreign materials to inject the liquid at a faster rate and for a shorter period of time than the liquid would be alternately aspirated. Generally, the oscillating liquid is maintained at a controlled volume range such that the same volume of liquid is continuously injected and aspirated to and from the localized area. Some of the oscillating liquid may however be lost due to seepage from the localized area or absorption into other body part areas or both. When such oscillating liquid is lost it may be necessary to add make-up oscillating liquid to the localized area to maintain effective amounts of the oscillating material therein. Adding fresh liquid may also enhance its effectiveness if such decreases over time, e.g., the solvent becomes saturated with solute or otherwise becomes inactivated. It is therefore particularly advantageous to have means for introducing the oscillating liquid to the localized area which comprise add-on means for increasing the volume of or adding to the volume of the oscillating liquid continuously with passage of time or intermittently as desired.

Exemplary advantageous applications of the method and means of the invention include homogeneous distribution of medications such as antibiotics or cancer combatants throughout the localized or target area to enhance their surface contact or absorption. The method would enhance local efficacy of hydrophobic therapeutic agents which are poorly miscible or soluble in an aqueous body liquid, e.g. bile. Especially beneficial applications of the methods and means of the inventions are to dissolve various undesirable materials that reside in localized areas of the body. Particularly, the methods and means of the invention are adaptable to facilitate dissolution of cholesterol stones and other types of gallstones, kidney and urinary tract stones; blockages in the digestive system, such as fecal impactions in the bowel lumen; and intravascular blood clots, atherosclerotic cholesterol plaque and other undesirable matter in the arterial system of the body.

In accordance with the method of the invention undesirable matter residing within a localized area of the patient's body may be dissolved by introducing a therapeutic dissolving agent to the localized area wherein the matter to be dissolved resides. The therapeutic dissolving agent is agitated by introducing an oscillating liquid to the localized area in an amount effective to distribute the dissolving agent delivered to the desired area and facilitate the dissolution of the undesirable matter residing in the localized area. Matter to be dissolved to which the present methods are particularly applicable include gallstones, kidney stones, blockages within the digestive system, cholesterol plaque, blood clots and other potentially soluble arterial blockages. The localized area wherein the undesirable material resides may be in the biliary tract, the gallbladder, the kidney, the liver, the bile duct, the intestine, arteries or other body space. In preferred embodiments of methods for dissolving undesirable matter in a localized area the oscillating liquid comprises a therapeutic dissolving agent. Such dissolving agents may be, for example, mono-octanoin or methyl tertiary butyl ether for dissolving gallstones, mineral oil or stool softeners for dissolving fecal blockages; mono-octanoin or methyl tertiary butyl ether for cholesterol plaque; and enzymes for dissolving blood clots.

Preferred pump means for distributing and stirring a therapeutic dissolving agent in a localized area of the patient's body can comprise combined liquid injecting and aspirating means which are capable of injecting and aspirating an effective volume of oscillating liquid. The injecting and aspirating means will generally be in a pump form. The pump means preferably comprise adjusting means to control the volume of the oscillating liquid and maintain it at a level that is effective to provide the desired agitation and distribution of the therapeutic agent or dissolving of undesirable matter within a localized area. Particularly, preferred pump means comprise separate adjusting means to control the rate of injection and aspiration independently in order to achieve the most efficient distribution parameters which might vary for the type of therapeutic agent being distributed, the body part into which the oscillating liquid is introduced and other subjective factors. The pump means preferably comprise forward flow add-on means which are capable of increasing or maintaining the volume of the oscillating liquid being introduced into the localized area. Add-on means are particularly desirable when it is possible that some of the oscillating liquid may be lost in the localized area of the body by seepage or absorption into other parts of the body.

In particularly preferred embodiments of the pump means of the invention, the pump means would provide for continuous stirring and optional flow increases during the distributing operations.

In applications of the pump means of the invention where strong solvents are utilized for therapeutic treatments it is desirable for pump means to comprise solvent resistant components. Suitable solvent resistant components are, for example, metal, e.g. stainless steel and fluorine containing resins such as Teflon brand fixtures.

Since the pump means are applied in medical situations where sterilization is an important factor the pump means are preferably comprised of sterilizable components which may be broken down from the pump and subjected to sterilization procedures as would be known to those skilled in the art.

The pump means also preferably comprise transparent components that permit outside viewing of the circulation of the oscillating liquid such that the therapeutic operation can be monitored. Suitable transparent components would be those comprised of acrylic materials such as Plexiglass brand acrylics More specific description of preferred embodiments of the method of the invention is set out in the following examples of the method of the invention as applied to dissolving foreign materials in a localized area of a patient's body. More particularly, the examples are concerned with the dissolution of gallstones by introducing an oscillating liquid in vivo to a localized area wherein the gallstones reside such as the biliary tract or the gallbladder itself as demonstrated in both in vitro and in vivo trials. Appreciation for the pump means utilized and various other practical details of the methods of the invention can be gained by review of the examples. The example section also contains comparative data which illustrates the effectiveness of the methods of the invention for dissolving gallstones in vivo versus conventional methods wherein no agitation and increased diffusion of the therapeutic dissolving agent is provided.

EXAMPLES

Examples 1-4

Examples 1-4 relate to in vitro examples of the methods of the invention for dissolving gallstones. The results of these examples and comparative (comp.) examples are listed in Table I.

Methods

A model bile duct consisting of glass tubing of a size and configuration representative of a human bile duct with a T-tube in place was developed.

Porcine bile was perfused through this glass tube of 12 mm internal diameter having a 3 mm outlet. Monooctanoin (MO) was introduced via a 16 French T-tube inserted through a side port, and a stone was placed 2 to 3 cm downstream from the distal arm of the T-tube in the model bile duct. Perfusions were performed at 37° C. and stones weighed at 12 or 24-hr intervals; studies were done in triplicate using stones containing 87% cholesterol, weighing 130±20 mg (M° SD) and taken from a single patient. Stone dissolution was determined during MO perfusion at 5 and 10 cc/hr with bile flow of 450 cc/24 hr. To study the effects of increased exposure of the stones to MO, bile was excluded from the system by using a balloon catheter to remove the bile present in the system or stirring was induced, or both. Stirring was accomplished through the T-tube by infusion (injection) and aspiration of 0.8 ml of MO as an oscillating liquid every 1-2 seconds using an automatic pump.

The results of the above trials are listed in the following Table I.

TABLE I

| Example | Stirring (Injecting & Aspirating) | Solvent | MO Flow Rate (ml/h) | Days to 50% Dissolution of the stone |
| --- | --- | --- | --- | --- |
| 1 | Yes | MO alone | 5 | .3 (±.03) |
| 2 | Yes | MO alone | 10 | .3 (±.01) |
| 3 | Yes | MO plus bile | 5 | .9 (±.1) |
| 4 | Yes | MO plus bile | 10 | .8 (±.01) |
| Comp. 1 | No | MO alone | 5 | 1.3 (±.07) |
| Comp. 2 | No | MO alone | 10 | .9 (±.07) |
| Comp. 3 | No | MO plus bile | 5 | 4.1 (±1.1) |
| Comp. 4 | No | MO plus bile | 10 | 4.7 (±1.4) |
| Comp. 5 | No | Bile alone | 0 | * |

*Use of bile alone resulted only in 3% dissolution after 6 days.

Examples 5 & 6

Examples 5 and 6 relate to in vivo examples of the methods of the invention carried out in days for dissolving human gallstones. The results of these examples and a comparative example are listed in Table II.

Methods

Each of 9 dogs had 3 human gallstones and the pigtail end of a 5 Fr. polyvinyl catheter implanted into the gallbladder. All 27 stones were from the same patient, 94% cholesterol and 189-238 mg in weight. After a 10 day recovery period 3 groups of 3 dogs each were studied. Comparative Example 5: Methyl tertiary butyl ether (MTBE) (20 ml) was instilled into the gallbladder then replaced hourly without stirring. Example 5: MTBE (20 ml) was instilled then continuous stirring was produced by alternate injection and aspiration of 5 ml in 30 second cycles. Example 6: MO (20 ml) was instilled and stirring was performed using the same volume and cycle frequency as Example 5. Stone size was determined every two hours by cholecystogram and complete dissolution confirmed by autopsy.

Stirring in Examples 5 and 6 was accomplished by oscillating and agitating effective amount of solvent with an alternating aspiration and (injection) pump.

The volume range for aspiration and injection is adjustable from essentially 0 up to 15 cc. Both aspiration and injection volumes were identical. The rate of aspiration and injection were independently variable. The rate of injection could be independently adjusted from essentially 0 to a maximum injection of the full 15 cc within 4.8 seconds. The rate of aspiration can be independently set up to a maximum rate of aspiration of the full 15 cc over a period of 5 to 7 seconds. Since this is a continuous process, the number of aspiration-injection cycles per minute is dependent on the volumes and rates selected as well as the internal diameter of the lumen of the catheter used and the viscosity of the fluid. A very high level of continuous stirring (turbulence), however, can be accomplished within a wide range of conditions.

The solvent (MBTE or MO) is introduced into the gallbladder by percutaneous transhepatic catheter placement whereby the catheter is attached to the pump by a syringe. The syringe is easily removable for cleaning or sterilization and the plunger has exchangeable gasket rings allowing for the use of Teflon coated rings which are quite resistant to all solvents including methyl tertiary butyl ether. Additionally a constant infusion inlet is located on the syringe which with the addition of a one-way flow valve, e.g. a ballbearing ball valve, allows for a constant flow simultaneous with active stirring.

The results of Examples 5 and 6 and comparative Example 5 are summarized in the following Table II.

TABLE II

| Example | Stirring (Injecting and aspirating) | Solvent | Complete Stone Dissolution (hours) |
|---|---|---|---|
| 5 | Yes | MBTE | 5.3 ± 0.7 |
| 6 | Yes | MO | * |
| Comp. 5 | No | MBTE | 11.3 ± 2.9 |

*MO achieved only 33% stone dissolution after 60 hours even with stirring.

Example 7

Example 7 is carried out in a manner similar to Example 5 except humans are used as the in vivo subjects and the following procedure is followed.

A biliary catheter is placed either percutaneously, transhepatically into the gallbladder, or endoscopically retrograde into the cystic duct leading to the gallbladder. After aspiration of bile from the gallbladder, 5–15 ml of MTBE is infused into the gallbladder containing stones. The solvent and any residual bile are agitated by aspiration and infusion using the pump as in Example 5. Stone dissolution is monitored by infusion of radial opaque contrast media via the catheter and after completion of stone dissolution the catheter is removed leaving the gallbladder intact The results of Example 7 would be similar to those of Example 5 in terms of approximate time for stone dissolution utilizing MBTE as solvent with stirring.

DISCUSSION

Table I illustrates the in vitro effectiveness of injecting (infusing) and aspirating a solvent to produce oscillating liquid further capable of agitating and distributing solvent for improved dissolution of gallstones. Injecting and aspirating proved to increase the effectiveness of the solvent on dissolution of gallstones by at least threefold.

Table II illustrates the in vivo effectiveness of injecting (infusing) and aspirating a solvent to produce oscillating liquid further capable of agitating a solvent in vivo to aid in distributing the solvent for improved dissolution of gallstones. Table II also illustrates the additional effectiveness of MBTE over the currently used MO solvent.

Table I also illustrates the effectiveness of excluding bile from a system when mono-octanoin is employed as a solvent. While such exclusion enhances stone dissolution, it has certain practical limitations as would be known to one skilled in the art. The enhancement of bile removal is overshadowed, however, by the improved results achieved with MBTE as the solvent without requiring bile removal.

The scope of the present invention is not limited by the description, example and suggested uses herein, and modifications can be made without departing from the spirit of the invention. For example, the methods and means of the invention can be adapted to the treatment of arterial blockages to dissolve the material residing therein or to distribute a cancer combatant drug in localized area where cancer has been found, to improve the effectiveness of the combatant in the area. Thus, it is intended that the present invention cover the modifications and variations of this invention provided they come within the scope of the appended claims and their equivalents.

What is claimed is:

1. A method for distributing a therapeutic agent in a localized area of a patients body comprising
    oscillatingly introducing effective amounts of said therapeutic agent to said localized area with an oscillating liquid by alternately injecting and aspirating effective amounts of said oscillating liquid so as to first distribute by agitation said therapeutic agent in said localized area and then remove said therapeutic agent therefrom
    said therapeutic agent being either a hydrophobic solvating agent designed to dissolve undesirable matter residing in said localized area or a drug designed to have medicating effect in said localized area.
2. The method of claim 1 wherein the oscillating liquid comprises the therapeutic agent.
3. The method of claim 1 wherein the therapeutic agent is introduced to the localized area separately from the oscillating liquid.
4. The method of claim 1 wherein the oscillating liquid is introduced by means comprising a combined aspirating injecting pump.
5. The method of claim 1 wherein the liquid is injected at a faster rate and shorter period of time than the liquid is alternately aspirated.
6. The method of claim 1 wherein the oscillating liquid is maintained in a controlled volume range whereby make up liquid can be introduced to the localized area to maintain the effective amount of oscillating liquid.
7. A method for distributing a liquid therapeutic dissolving agent in a localized area of a patients body to facilitate dissolving and thereby removing undesirable matter residing therein comprising
    oscillatingly introducing effective amounts of said therapeutic agent to said localized area by alternately injecting and aspirating said therapeutic agent along or with an oscillating liquid to and from said localized area so as to thereby distribute by agitatiion said thereapeutic agent in said localized area and contact and dissolve said undesirable matter and remove the same from said localized area.
8. The method of claim 7 wherein the matter to be dissolved is selected from the group consisting of gall stones; kidney stones; blockages within the digestive system; cholesterol plaque and blood clots.
9. The method of claim 8 wherein the matter to be dissolved is gallstones.
10. The method of claim 7 wherein the localized area of a patients body is selected from the group consisting of:
    gallbladder; kidney; liver; biliary tract; intestine; and artery.
11. The method of claim 10 wherein the localized area of a patients body is the biliary tract.
12. The method of claim 7 wherein the oscillating liquid comprises the therapeutic dissolving agent.
13. The method of claim 12 wherein the oscillating liquid is introduced by means comprising a combined aspirator-injector pump.
14. The method of claim 13 wherein the oscillating liquid is maintained in a controlled volume range whereby make-up liquid can be introduced in the localized area to maintain the effective amount of oscillating liquid therein.
15. The method of claim 13 wherein the oscillating liquid is injected at a faster rate and for a shorter period of time than the oscillating liquid is alternately aspirated.

16. The method of claim 7 wherein the therapeutic dissolving agent is selected from the group consisting of mono-octanoion and methyl tertiary butyl ether.

17. The method of claim 12 wherein the oscillating liquid is introduced to the localized area by means selected from the group consisting of percutaneous transhepatic catheter placement; endoscopic retrograde biliary catheter placement; and placement of a t-tube into the localized area by surgical means.

18. The method of claim 17 wherein the catheter means comprise a fine needle or flexible catheter.

19. A method for distributing a liquid therapeutic dissolving agent in the biliary tract of a patient to dissolve gallstones residing therein comprising oscillatingly introducing effective amounts of said therapeutic dissolving agent to said biliary tract by alternately injecting and aspirating said therapeutic agent along or with an oscillating liquid to and from said biliary tract so as to thereby distribute by agitation said therapeutic agent in said biliary tract and contact and dissolve said gallstones and remove the same form said biliary tract.

20. A method as in claim 19 wherein said oscillating liquid comprises said therapeutic dissolving agent.

21. A method as in claim 20 wherein said oscillating liquid is introduced by means comprising a combined aspirator-injector pump.

22. A method as in claim 20 wherein said oscillating liquid is selected from the group consisting of mono-octanoin and methyl tertiary butyl ether.

23. A method as in claim 22 wherein said oscillating liquid is methyl tertiary butyl ether.

24. A method for distributing a liquid therapeutic dissolving agent in the gallbladder of a patient to dissolve gallstones residing therein comprising oscillatingly introducing effective amounts of said therapeutic dissolving agent to said gallbladder by alternately injecting and aspirating said therapeutic agent alone or with an oscillating liquid to and from said gallbladder so as to thereby distribute by agitation said therapeutic agent in said gallbladder and contact and dissolve said gallstones and remove the same from said gallbladder.

25. A method as in claim 24 wherein said oscillating liquid comprises said therapeutic agent.

26. A method as in claim 25 wherein said oscillating liquid is introduced by means comprising a combined aspirator-injector pump.

27. A method as in claim 25 wherein said oscillating liquid is selected from the group consisting of mono-octanoin and methyl tertiary butyl ether.

28. A method as in claim 27 wherein said oscillating liquid is methyl tertiary butyl ether.

* * * * *